Figure 1:
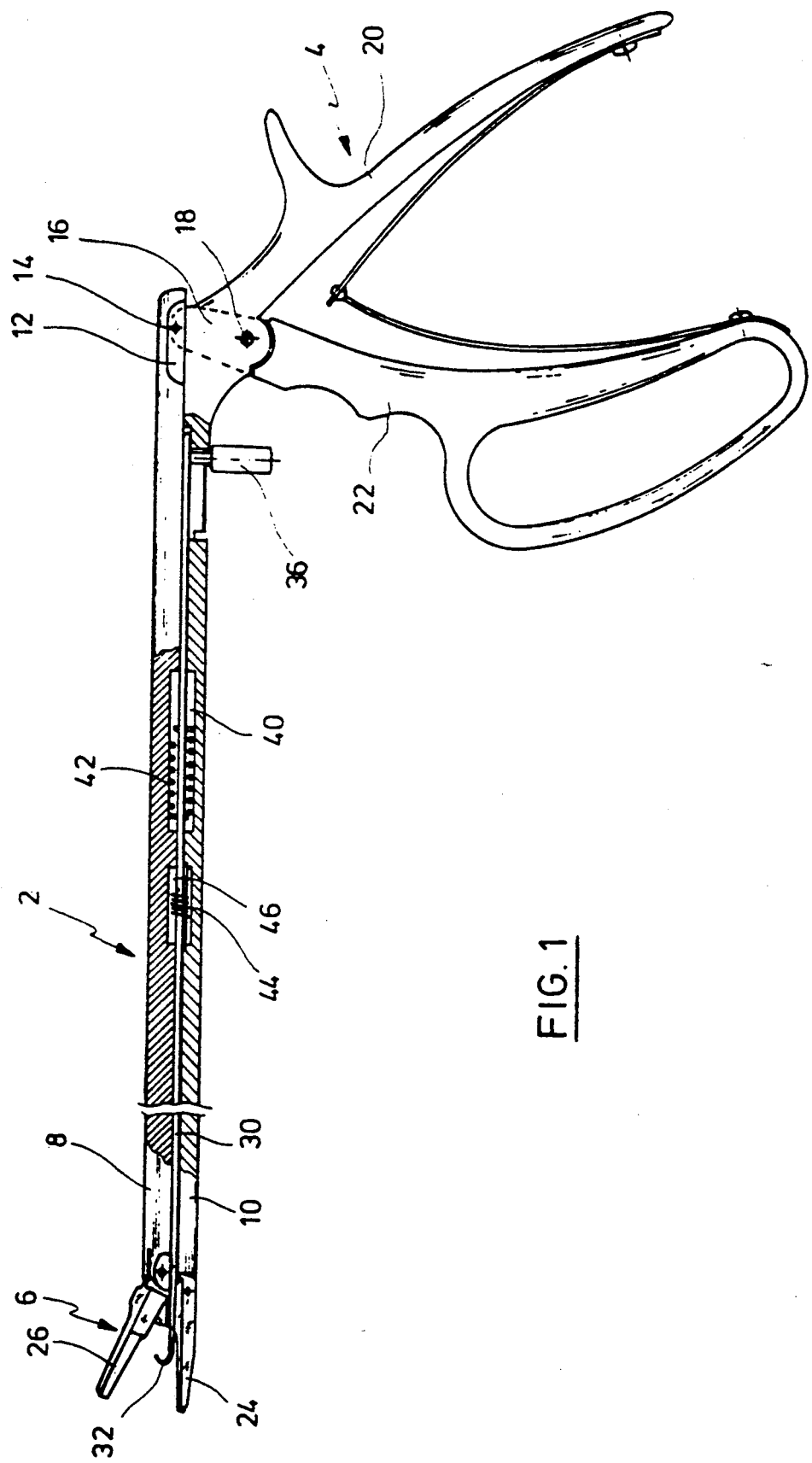

United States Patent [19]
Troidl et al.

[11] Patent Number: 5,156,608
[45] Date of Patent: Oct. 20, 1992

[54] CLIP APPLICATOR FOR LIGATURE CLIPS

[76] Inventors: Hans Troidl, Ostmerheimer Strasse 200, 5000 Koln 91; Ahmad Al-Jaziri, In der Rosenau 8, 5000 Koln 90; Harald Heidmuller, Heidenrichstrasse 10, 5000 Koln 80; Helmut Kaufmann, Giessstrasse 9, 7200 Tuttlingen, all of Fed. Rep. of Germany

[21] Appl. No.: 724,055

[22] Filed: Jul. 1, 1991

[51] Int. Cl.⁵ .............................................. A61B 17/00
[52] U.S. Cl. ..................................... 606/142; 227/901
[58] Field of Search ........................ 606/142, 144, 1; 227/901

[56] References Cited

U.S. PATENT DOCUMENTS

| | | | |
|---|---|---|---|
| 3,463,156 | 8/1969 | McDermott | 606/142 |
| 3,777,538 | 12/1973 | Weatherly et al. | 606/142 |
| 3,954,108 | 5/1976 | Davis | 606/158 |
| 4,064,881 | 12/1977 | Meredith | 606/142 |
| 4,957,498 | 9/1990 | Caspari et al. | 606/144 |

FOREIGN PATENT DOCUMENTS 2044108 10/1980 United Kingdom ................ 606/142

*Primary Examiner*—Gary Jackson
*Attorney, Agent, or Firm*—Paul A. Coletti

[57] ABSTRACT

The invention relates to a clip applicator for ligature clips, particularly for laparoscopic operations, comprising a tubular rod system, at whose one end is provided a two-part, scissor-like handle and at whose opposite end are provided jaws for receiving a clip, in which one handle part of the scissor-like handle is fixed to one part of the rod system, while the other handle part brings about about a closure of the jaws if the two handle parts are moved relative to one another, against spring tension, about their pivot axis located below and at right angles to the longitudinal axis of the tubular rod system, characterized in that in the tubular rod system (2) is movably arranged a restoring wire (30), whose front or proximal end (32) is constructed in hook-like manner and in the inoperative position is positioned with an upwardly open hook alongside the jaws (24, 26), while the rear or distal end (34) of the restoring wire (30) is connected in the vicinity of the handle (4) to an operating lever (36) projecting out of the tubular rod system (2).

8 Claims, 2 Drawing Sheets

CLIP APPLICATOR FOR LIGATURE CLIPS

The invention relates to a clip applicator for ligature clips for an endoscopic clip applicator, particularly for laparoscopic surgical operations in accordance with the preamble of the main claim.

Such clip applicators are e.g. used according to Akt. Urol., 15 1984, pp.126 to 128 eg. in a construction in accordance with the company publication OP-INST 9 A of the Storz Company, Edition 5(89), in order to ligate vessels, such as e.g. an aorta with clips made from metal, such as silver or titanium, as well as resorbable material.

Although in many surgical fields clips are widely used due to their speed of application and accessibility in connection with difficultly accessible vessels in place of conventional ligature technology using suture material, in laparoscopic surgery difficulties have been encountered with the known clip applicators in that it is not possible to get hold of the vessels to be ligated and introduce same into the clip area from the outside, e.g. assisted by finger manipulation and also as a result of the fact that in laparocscopy the spatial identification of the vessels to be ligated is naturally reduced. For example, it is difficult to get hold of the cystic duct and cystic artery, particularly in the case of obese patients in cholecystectomy.

In order to obviate these difficulties, a novel clip applicator of the aforementioned type is produced, which is constructed in accordance with the characterizing part of the main claim and special embodiments are given in the subclaims.

It has surprisingly been found that the vessel in question can be drawn into the clip located in the jaws by the provision of a restoring or return wire which can be moved backwards and forwards. In a particularly preferred embodiment the restoring wire is also pivotable to a limited extent about its longitudinal axis.

In a particularly preferred embodiment the movement backwards and forwards and/or the rotating movement of the restoring wire can be performed in opposition to the tension of a spring, so that, under spring action, the restoring wire can be brought back into its starting position, namely in the immediate vicinity of the jaws.

The invention is described in greater detail hereinafter relative to the drawings, wherein show:

FIG. 1—an overall view of the clip applicator according to the invention.

Figure 2:
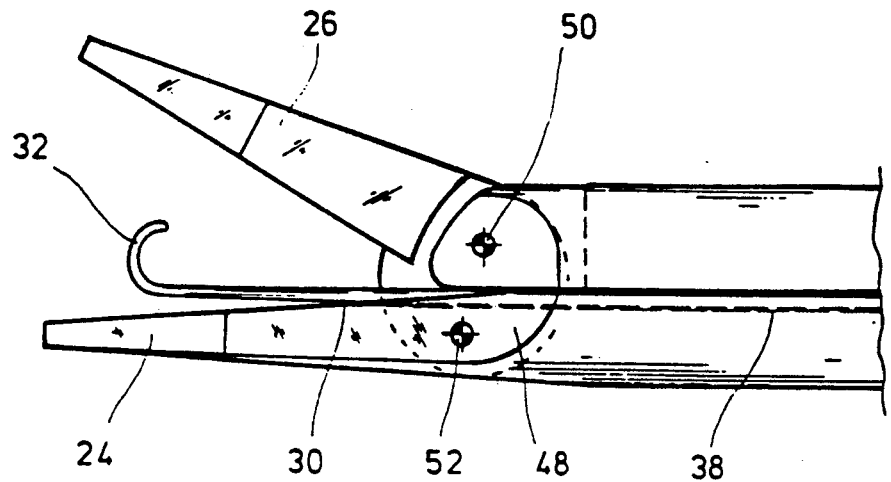

FIG. 2—a detail of the jaw construction of the clip applicator according to the invention.

Figure 3:
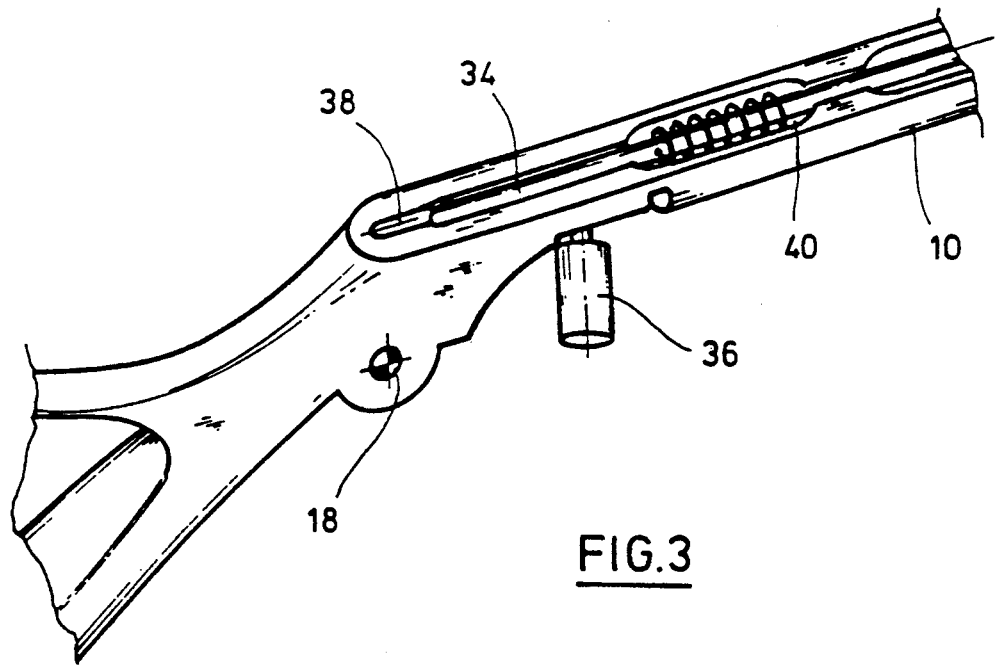

FIG. 3—a view of the handle-side end of the clip applicator according to the invention.

The clip applicator shown in FIG. 1 comprises a rod system 2, a distal handle 4 and a proximal jaw 6, the terms distal and proximal relating to the patient's body.

The rod system 2 comprises an upper rod 8 and a lower rod 10, both of which have a semicircular cross-section and whose flat sides are so arranged with respect to one another that they form a tubular rod system. The upper rod 8 and the lower rod 10 are guided in their limited axial movement, by a hinge connection in the vicinity of the jaw 6 and a corresponding hinge connection in the vicinity of the handle 4, as will be described in detail hereinafter.

It is also possible to guide the upper rod 8 and the lower rod 10 by corresponding T-shaped or L-shaped projections in correspondingly shaped slots, or although in a preferred embodiment guidance by means of a pivotable connecting element 48 in the vicinity of the jaw 6 and a corresponding connecting element 16 in the handle area is completely adequate.

In the embodiment shown in FIG. 1, the inventively essential restoring wire 30 is located in a slot 38 in the lower rod 10 and runs in the longitudinal direction of the latter. The restoring wire 30 has a hook-shaped end 32 with an upwardly open hook, whilst the rear end 34 of the restoring wire terminates in the vicinity of the handle 4 and passes into an operating lever 36, which projects out of the rod system 2. As desired, the operating lever 36 can be given a pin or stud-like construction, but can also be annular.

The restoring wire 30 is axially displaceable by means of the operating lever 36 and in a preferred embodiment can be returned to its inoperative position by a return spring 42, which is located in a chamber 40 for said spring in the lower rod 10.

In a preferred embodiment the restoring wire 30 can be rotated out of its starting position with the upwardly open hook about its longitudinal axis by up to approximately 45° on either side. For this purpose in a further chamber 44 is provided a restoring spring 46, which returns the hook to its vertically directed inoperative position.

In the construction of the handle part shown in FIG. 1, the outer handle part 20 is connected in materially integral manner with the lower rod 10 of the handle 4, whilst inner handle part 22 pivotable about a pivot pin 18 of the handle part is connected to a connecting element 16, which is in turn connected about a linch-pin 14 to a nose 12 of the upper rod. Thus, on tightening the inner handle part 22 there is a forward, axial movement of the upper rod 8, accompanied by a reliable guidance of the particular rod.

The jaw construction shown in detail in FIG. 2 is constructed in the same way. To make understanding easier therein, the spread-apart position of the jaws is shown in a somewhat exaggerated form. For laparoscopic operations, in which the apparatus is introduced through a trocar, the upper edge of the upper jaw 26 must be aligned with the upper edge of the upper rod 8 in the spread-apart position.

The lower jaw 24 is constructed in materially integral manner with the lower rod 10, in which is provided the slot 38 for the restoring wire 30. The upper jaw 26 is pivotably connected by means of a linch-pin 50 to the end of the upper rod 8, namely by means of a connecting element 48, which is anchored by means of a further linch-pin 52 in the lower rod 10.

On compressing the outer handle part 20 and the inner handle part 22, the upper rod 8 moves forwards or in the proximal direction so that the upper jaw 26 closes and compresses the previously inserted clip.

As shown in FIG. 3, the rear end 34 of the restoring wire 30 is connected to an operating lever 36, which can be operated in opposition to the tension of the return spring 40 and is also pivotable about its longitudinal axis in opposition to the tension of the restoring spring 44.

When using the applicator, an open oriented clip is firstly inserted between the lower jaw 24 and the upper jaw 26 and following the corresponding insertion of the clip applicator into the operating area the restoring wire 30 is advanced until it grips the appropriate vessel, optionally accompanied by a rotating of the hook. By a corresponding manipulation of the operating lever 36, it is brought together with the grasped vessel into the mouth area of the jaw 6 and by corresponding handle operation the clip is placed around the vessel.

The endoscopic clip applicators according to the invention cannot only be used for cholecystectomy, but are in general always advantageous when it is necessary to clamp off vessels, such as e.g. in selective, proximal vagotomy, when mobilizing the esophagus, in hepatectomy, in lobectomy and segment resection, in lymphadenectomy and also for ligatures in pelviscopy.

We claim:

1. Clip applicator for ligature clips, particularly for laparoscopic operations, comprising a tubular rod system, with a proximal end and a distal end, at whose proximal end is provided a two-part, scissor-like handle and at whose distal end is provided jaws for receiving a clip, in which said handle is associated with said jaws to bring about a closure of the jaws if the two handle parts are moved relative to one another, characterized in that the tubular rod system contains a restoring wire, whose distal end is constructed in the form of a hook and in the operative position is positioned with said hook protruding from said jaws, whereas the proximal end of the restoring wire is connected in the vicinity of the handle to an operating lever projecting from said tubular rod system.

2. Clip applicator according to claim 1, characterized in that the restoring wire is forced into an inoperative position under the action of a return spring and on advancing the operating lever in the proximal direction can be moved over and beyond the jaws to said operative position.

3. Clip applicator according to claim 1, characterized that the restoring wire is rotatable about its longitudinal axis.

4. Clip applicator according to claim 1, characterized in that the restoring wire can be rotated when in its operative position with an upwardly directed hook by up to 45° on either side about its longitudinal axis.

5. Clip applicator according to claim 4, characterized in that the restoring wire can be rotated out of its operative position in opposition to the tension of a restoring spring.

6. Clip applicator according to claim 2, characterized in that the return spring for the axial return of the restoring wire to its inoperative position is fitted in recesses or chambers created in said lower rod.

7. Clip applicator according to claim 1, characterized in that
   (a) the rod system comprises an upper rod and a lower rod, both which have a semicircular cross-section and with flat sides resting upon one another and are axially movable to a limited extend,
   (b) one handle part of the scissor-like handle is connected to said lower rod below the longitudinal axis of the rod system and at right angles to said axis, and said handle has a pivot pin about which is pivotable the second handle part connected above said axis to the upper rod,
   (c) said jaws comprise a lower jaw, which is shaped in materially integral manner onto the distal end of the lower rod and an upper jaw, which is so pivotably fixed to the upper rod, such that in the case of a parallel displacement of the upper rod, said upper jaw can be brought int a closed position against said lower jaw by bringing said handle parts into proximity of one another; and,
   (d) the restoring wire is guided in an axial slot or bore in said lower rod and is provided at its proximal end with an operating lever.

8. Clip applicator according to claim 7, characterized in that the restoring wire is guided in its proximal area by a first axial slot or bore in the upper rod and in its distal area by a second slot or bore in the lower rod guided into the first axial slot or bore.

* * * * *